United States Patent [19]

Lentzen

[11] Patent Number: 5,012,681
[45] Date of Patent: May 7, 1991

[54] SAMPLING PROCEDURES AND PROTECTIVE LAYERS FOR THE PRESERVATION OF PARTICULATES OBTAINED BY FILTER COLLECTION AND IMPINGEMENT OPERATIONS

[76] Inventor: Donald E. Lentzen, 305 Oakridge Rd., Cary, N.C. 27511

[21] Appl. No.: 356,624

[22] Filed: May 19, 1989

Related U.S. Application Data

[63] Continuation of Ser. No. 82,028, Aug. 5, 1987, abandoned.

[51] Int. Cl.$^5$ .............................................. B01D 50/00
[52] U.S. Cl. .................. 73/863.23; 73/864.91
[58] Field of Search ................ 73/864.91, 863.23; 55/270

[56] References Cited

U.S. PATENT DOCUMENTS

| | | |
|---|---|---|
| 1,824,537 | 12/1931 | DeCorrevont . |
| 3,422,679 | 1/1969 | McGowan et al. . |
| 3,561,253 | 2/1971 | Dorman . |
| 3,877,878 | 4/1975 | Kerfoot et al. ............... 422/100 |
| 3,954,428 | 5/1976 | Marple et al. ............. 55/270 |
| 3,957,469 | 5/1976 | Nebash ..................... 55/270 |
| 3,966,439 | 6/1976 | Vennos ..................... 55/270 |
| 4,178,794 | 12/1979 | Jugle et al. ............... 55/270 |
| 4,277,259 | 7/1981 | Rounbehler et al. ........ 55/270 |
| 4,350,507 | 9/1982 | Greenough et al. ........ 73/863.23 |
| 4,426,214 | 1/1989 | Vandrish .................. 55/270 |
| 4,437,333 | 3/1984 | Hands .................. 73/863.23 X |
| 4,447,374 | 5/1984 | Tanaka . |
| 4,530,250 | 7/1985 | Gay et al. .................. 73/863.12 |
| 4,544,386 | 10/1985 | Trayford, III et al. ........ 55/270 |
| 4,550,591 | 11/1985 | Cox et al. . |
| 4,551,216 | 11/1985 | Argyo . |
| 4,586,389 | 5/1986 | Vincent et al. . |
| 4,590,792 | 5/1986 | Chiang . |

OTHER PUBLICATIONS

Lentzen et al., Proceedings of the 44th Annual Meeting of the Electron Microscopy Society of America, Aug. 10-15, 1986.

Lentzen et al., Abstract, American Industrial Hygiene Assn., Montreal, Jun. 2, 1987.

*Primary Examiner*—Hezron E. Williams
*Assistant Examiner*—Robert P. Bell
*Attorney, Agent, or Firm*—Ostrolenk, Faber, Gerb & Soffen

[57] ABSTRACT

A method for collecting a particulate sample from a gas or liquid particulate suspension on a substrate and keeping the collected particulate on the substrate in the same position and orientation as when it was initially collected. The substrate for collecting particulate may be covered with a coating or film that reacts with the substrate or the particulate and is optically and electron transparent. A coating or film may be placed over the collected particulate as well as, or instead of, the coating or film directly concerning the collecting substrate. A particulate sample sandwiched between two electron transparent coverings is suitable for analysis by electron microscopy.

13 Claims, 3 Drawing Sheets

SAMPLING PROCEDURES AND PROTECTIVE LAYERS FOR THE PRESERVATION OF PARTICULATES OBTAINED BY FILTER COLLECTION AND IMPINGEMENT OPERATIONS

This is a continuation of application Ser. No. 082,028 filed on Aug. 5, 1987 now abandoned.

FIELD OF THE INVENTION

The invention relates to protecting and preserving samples of particulate and microparticulate materials in the state exactly as they were collected. These field methods involve trapping, capping, coating, and in other ways fixing or covering the sampled materials in their deposited state for safe transport to an appropriate analytical facility. Protection is necessary at times for the preservation of a representative particulate distribution on the collection surface in consideration of the possible physical and/or electrostatic forces which may selectively disrupt or rearrange the placement of the particulate before analysis. Covering or fixing the sample helps document the sample validity and can facilitate subsequent analytical procedures.

BACKGROUND OF THE INVENTION

Suspensions of particulate materials in gaseous and liquid media are an important natural and man-made phenomenon. Smokes and paints are some familiar examples of these mixtures. Other examples include air samples to test for the presence and concentrations of asbestos, silica, cotton fibers, and coal dust. To further define these suspensions, it is usually necessary to analyze them qualitatively and quantitatively. One of the common methods for analysis of the gaseous or liquid media suspensions begins by separating the solids using a filtration operation. This process simplifies the analysis by collapsing the two phase, three-dimensional system into a one phase, two-dimensional system. The gas or liquid will be separated from the solid particulate, and a concentration of the particulate is achieved. The settling out or impingement of particulate results in a similar potential sample which has been selectively separated, when those methods are used. Materials retained on the filter or other deposition surface are then available for analysis by a variety of techniques that could not be employed while the particulate was suspended.

The retention of the captured material on the surface must be maintained during the sample's transport and other preparatory steps if meaningful analytical results are to be obtained from the filtration or impingement operations. While the first step in particulate collection has been carefully studied to reveal that the interception, impaction, electrostatic attraction, and van Der Waal force are primary deposition mechanisms, the forces for particle retention are not so well defined as to assure continued interaction under every condition the sample may encounter thereafter. Environmental changes can occur immediately after the sampling operation is concluded. The post-sampling conditions may potentially be as important as the conditions during filtration in producing a representative sample. For example, when the pressure differential on the filter is released, the fluid flow ceases and the particulate might become less tightly held to the collecting substrate. The static electric charge established during sampling may change. Evaporation may occur or hygroscopic actions may change surface tensions. For these reasons and others, the particle/filter or particle/surface interaction dynamics may be significantly altered thus affecting the distribution and/or retention of the particulate on the filter.

The mechanisms which maintain the particle in contact with the filter after the initial capture are electrostatic and molecular in nature unless the particulate is entrapped physically in the filtering media. These forces are relatively weak and are very apt to change if the sample is transported. In the transportation process, the sample will likely undergo a certain amount of mechanical shock, vibration, temperature change, humidity change, pressure change and electrostatic force transitions. Gravity may act as a positive or negative fact or in maintaining the particle contact. Carrying the sample upright at all times to its destination will reinforce the association but will not guarantee the sample integrity. Carrying the sample on the filter in any other orientation will be a negative factor in this particle/filter association. These same potentially disruptive effects are present on both filter and surface collected samples whatever the mode of transportation and regardless of the trip length. The only variable is the degree of disruption in a given instance. These stresses will dislodge the particulate if they individually or collectively exceed the particle attachment forces.

With the exception of some samples destined for X-ray analysis or impactor samples collected on greased plates, little attention is paid to insuring that the samples are fixed in place before committing them to the mail or the other transport system. Presently, tens of thousands of samples are at risk each year with only relatively passive attempts being made to protect them by attaching warning labels to the package such as "handle with care" or "this side up". When these requests are made, they may not be recognized in time or acknowledged fully and thus are not totally satisfactory solutions to this problem. Furthermore, a mere warning may not be sufficient protection to the materials while in shipment. Since the particulates in a sample are often microscopic in size, it would take a special microscopic survey of the filter and containment surfaces to possibly detect a displacement of a sample. Even then, proving a redistribution on the filter surface would be difficult. Obtaining a representative sample of the material is extremely important to the data interpretation and deductive conclusion part of any study, since: (a) only small portions of the filter may be analyzed and (b) large multiplication factors are applied to the portions analyzed to calculate the constitution of the entire sample. Any loss or addition of material to the section analyzed would be an error which would multiply proportionally.

Presently, particulate samples are coated with evaporated carbon or metal as the first step in the laboratory to fix them in place for the electron microscopy analytical process. Optical microscope samples are fixed to a slide/coverslip arrangement. However, fixing the sample at the laboratory may be too late for preserving the original particle distribution.

SUMMARY OF THE INVENTION

The present invention provides a method of collecting and preserving samples of particulate suspensions, wherein a film or coating is cast, or otherwise caused directly or indirectly, to cover a collecting substrate, such as a filter so that the collective or retentive capacity of the collecting substrate is enhanced. Examples of suitable films or coating include conductive coatings, adhesive films, and coherent coverings (such as carbon), which trap, sequester or in other ways secure the placement of particulate at or near the point of impact. The coatings or films may be chosen for electron transparency, optical transparency, reactivity to the collecting substrate or the particulate to be collected, or other properties useful in the sampling of particulate suspensions. Furthermore, the film or coating may act as an underlying base for conveying the particulate sample through its physical and chemical analysis, or the coating may be subsequently modified or even dissolved away.

The present invention also encompasses the procedure in which an additional film or covering is placed over the collected particulate to encase and protect the collected sample. The overlay may have self-adhesive properties to the underlying film. Alternatively, the overlay may be fixed by physical means or chemical bonds, by the addition of appropriate bonding compounds in liquid or vapor form. Radiant energy, such as heat and ultraviolet light may also be used to effect the bonds between the layers.

The film and coatings of the present invention may be prepared as part of a filter or collecting device to be taken into the field. Alternatively, the film or coating may be prepared separately, and then applied later.

In one embodiment, the overlaying protective film or coating may be layered directly on top of the collected particulate sample.

DETAILED DESCRIPTION OF THE INVENTION

Figure 1:
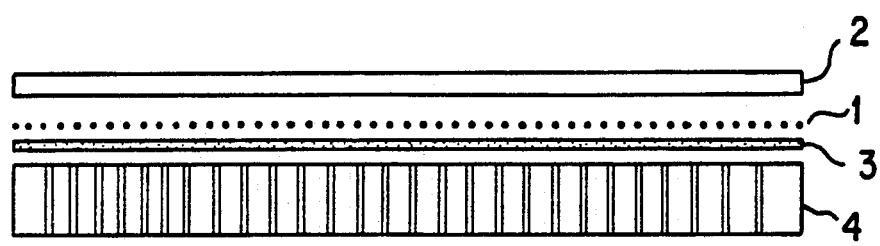
FIG. 1 shows particles sandwiched between two protective layers in accordance with the teaching of the present invention.
Figure 2:
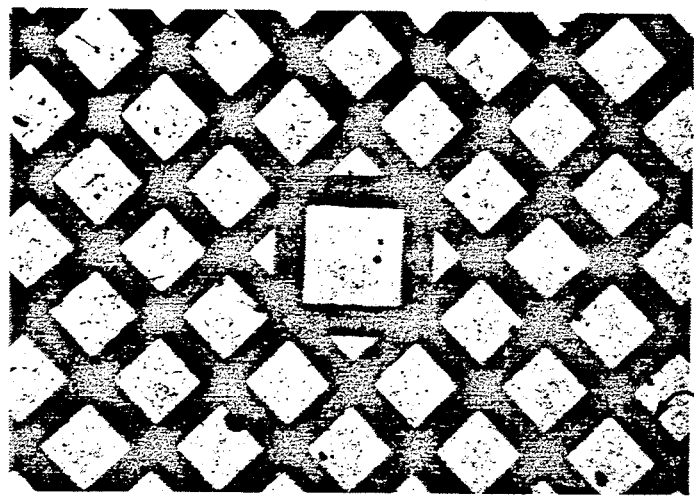
FIG. 2 is transmission electron microscopy image (at 100×magnification) of asbestos fibers between a carbon coat and a collodion film. A copper grid is included in the image.
Figure 3:
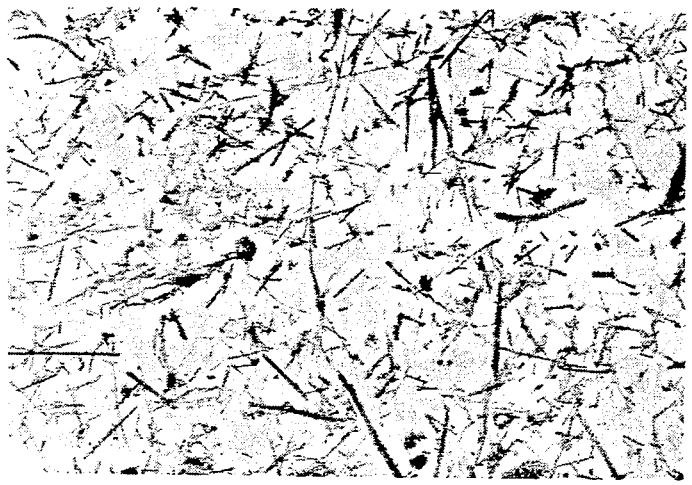
FIG. 3 is transmission electron microscopy image (at 10,000×magnification) of the same subject matter as FIG. 2. The magnification is large enough that the copper grid is no longer visible.
Figure 4:
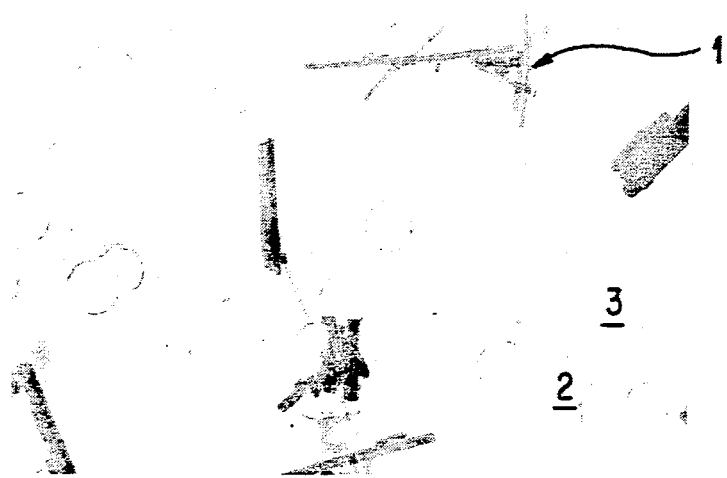
FIG. 4 is a transmission electron microscopy image (at 20,000×magnification) of the same subject matter as FIG. 3.
Figure 5:
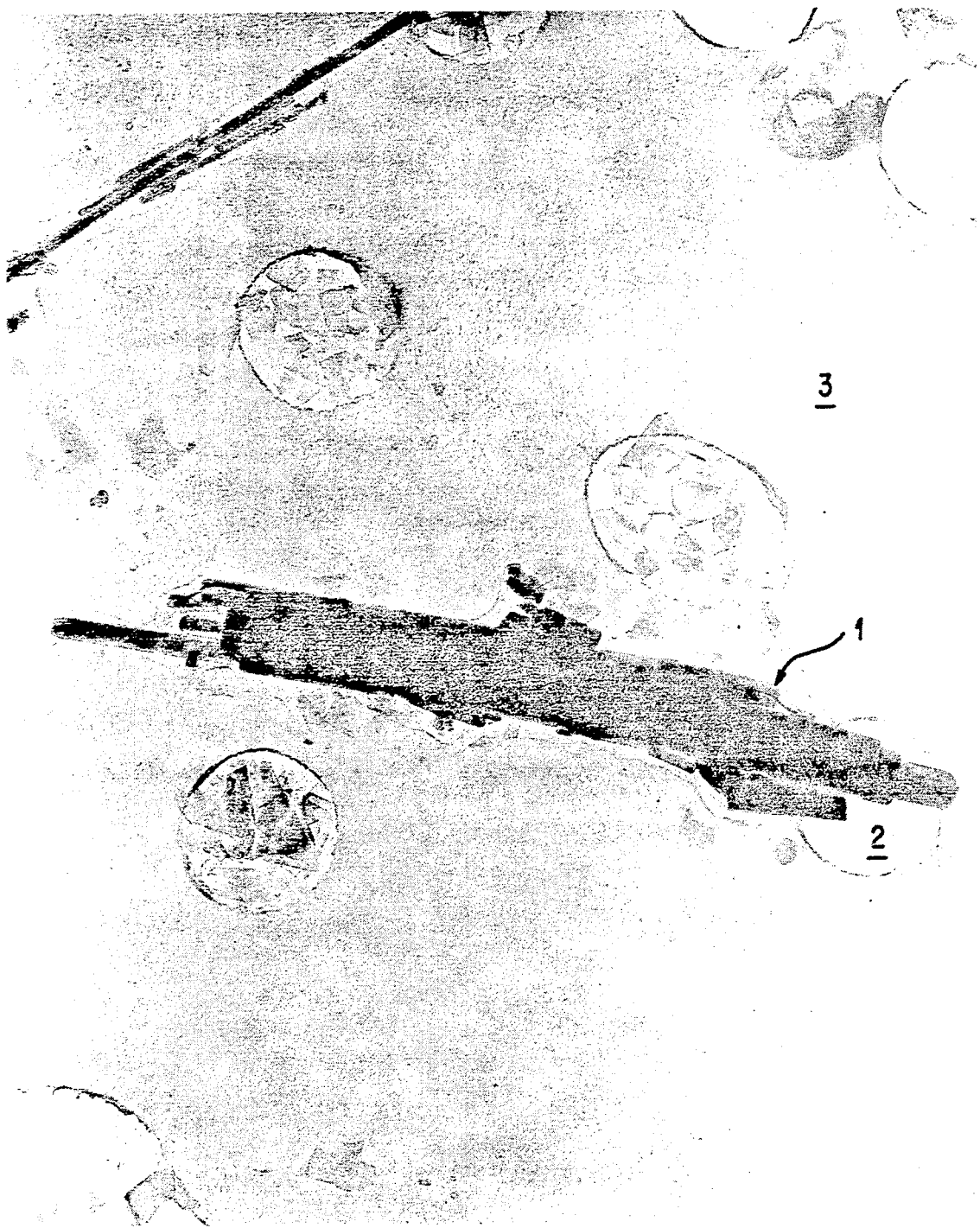
FIG. 5 is a transmission electron microscopy image (at over 100,000×magnification) of the same subject matter as FIG. 3.

According to the method of the invention, there are several ways to stabilize the particulate on the collecting substrate, thereby freezing conditions as they existed at the conclusion of the sampling phase. In general, the method involves the application of a protective cover or overlay to fix each particle in its position and deposition orientation on the collecting substrate. The collecting substrate may be a filter on which the suspended particulate has been drawn for deposit from a liquid or gaseous medium. The method may also pertain to particles which have settled on a solid surface, such as dry or wet atmospheric deposits on a leaf surface for acid rain studies. These particulates may be subsequently visualized using light or electron microscopy and analyzed for elemental composition or crystal lattice patterns. Organic compound identification may be achieved through infrared techniques and a variety of other analytical methods such as LAMMA (laser microprobe mass analysis). The type of covering and securing mechanisms chosen is dependent on the sample, the collection system used and the proposed analytical approach.

For those samples which are to be collected on filters, the particulate may be firmly attached to the underlying substrate by placing a cap of film or another type of cover over the sample at the completion of the sampling operation. For example, particulate collected on a cellulose ester acetate filter may be encased with transparent collodion, urethane or other film. The film may then be fixed to the filter by drawing a small amount of acetone vapors through the assembly, thus fusing the filter and film in a bonded unit with the particulate in between. In one embodiment of the present invention, acetone is dripped onto a backing filter which is set over the film, and then a slight vacuum is pulled through the filtering device. When the sheen is lost from the film, sufficient bonding has taken place. The filter does not lose its transparency after adding a liquid of similar refractive index or a solvent to collapse the filter/particulate/film sandwich structure. Thus optical transmission or reflected light microscopy may readily be conducted on these samples according to techniques well-known to those skilled in the art. If the cellulose ester filter is dissolved, using, for example, acetone as a solvent, then the sample can be examined with selected area electron diffraction.

For samples destined to be analyzed in the electron microscope, it is often advantageous to use a flat filter substrate such as polycarbonate filters. These filters may be precoated with an electron transparent layer of evaporated carbon or other applied substance. Next, the filter is used to collect the particulate and that material is fixed in place by overlaying an electron transparent layer of collodion or other uniform cover. The two films may be joined by introducing a layer of decane. Other alkanes ($C_8$-$C_{18}$) can be used, which are (a) miscible (i.e., will not react and form an opaque precipitate with the solvent used to subsequently dissolve the polycarbonate filter) and (b) hold the two films together. (For NUCLEOPORE ® polycarbonate filters, the solvent is chloroform or carbon tetrachloride.) The two films may be joined by physical surface tension as well as chemical bonding. At this point, the sample is safely preserved for transport and conventional laboratory handling activities, because it is effectively laminated between two integral surfaces.

Solid surfaces, for example, a leaf or rock, may be covered with a film, wetted with a penetrating liquid, which effectively transfers the film from its frame to the top of the object sampled. This sort of sample is commonly analyzed by reflected light microscopy or scanning electron microscopy. Certain types of film material are drapable over the trapped particulate by partially dissolving or softening the overlay at the time of film placement. These film types are particularly useful in this application.

In one embodiment of the invention, the film selected is dissolved away in the laboratory prior to analyzing the sample.

Production of the overlay films may be effected by several different methods. If the monomer used is not soluble in water and has a lower specific gravity, it may be cast onto the water surface where solvent evaporation or polymerization take place. The film thickness can be varied by the concentration of the casting solution or the effective surface area on which it is cast, using methods well-known to those in the art. Collodion in amyl acetate is a common example of this technique which has been done on a smaller scale to coat electron microscope grid surfaces. Systems other than collodion and surfaces other than water can also be used. As an example, the dip pickup of a monomer of a cationic ultraviolet-light curable polymer, such as CYRACURE ® (Union Carbide Corp., Danbury, Conn.) on a frame can be made, followed by photoinitiated polymerization of the adhering solution film on the frame.

The films themselves need not be made at the site they are to be used. They can be precast in the laboratory and they are protected from extraneous particulates and physical damage. Electron transparent overlay films of 37 mm diameter have been packed and shipped across country by common carrier with a good success rate of survival.

A number of materials are useful for the embodiments of the invention employing a film or coating on the collecting surface. For example, adhesive and electrically conductive coatings are suitable. Conductive coatings include metals coatings, formed by evaporating metal off a very hot surface, and certain polymers, such as doped polyacetylene. In addtion to polyacetylene treated with oxidizing or reducing agents, polyphenylene or polypyrrole exhibit significant conductivity. A coherent film, that is, substantial yet electron and/or light transparent depending on application, are also suitable for use in connection with the present invention. An example of a coherent coating is a carbon coating.

The invention will be further illustrated in the following example:

EXAMPLE

This example illustrates the use of the method and protective overlays of the present invention to protect air samples, which have been collected on NUCLEOPORE ® polycarbonate filter (Nucleopore, Inc., Pleasanton, Calif.) for transmission electron microscopy analysis of asbestos fibers. As described, the freshly-taken sample is enveloped between two electron transparent films.

First, approximately 40 nm of carbon is vacuum deposited on a NUCLEOPORE ® polycarbonate filter of the chosen diameter and pore size. The carbon is deposited onto the collection side of the filter without polymerizing the polycarbonate by overheating. The carbon coat is thin enough so that portions of the carbon coat will fall through the pores of the NUCLEOPORE ® polycarbonate filter when a vacuum is applied as part of the sampling procedure. The coated filter is then loaded into the sampling cassette under clean room conditions and stored for transport to the field.

Next, an electron transparent film of collodion in amyl acetate is cast on a clean water surface. A portion of the cured film that is even, colorless, and flawless is selected to pick up on the base end of the middle piece of a second cassette or on a frame of slightly less diameter to use as an insert directly into the sampling cassette. More than one attempt may be necessary to produce a film having the desired characteristics until the person casting the film develops the necessary level of skill. The residual water from the film is then evaporated before the cassette is loosely reassembled for its safe transport to the field.

Once in the field, the filter-containing cassette unit is attached to the sampling train. Next, the desired amount of airborne particulate is collected on the filter; the cassette should be oriented in an upright position before the vacuum pump is turned off. The sample cassette cowling is removed and gently replaced with a film-containing middle piece from the second cassette. The cassette middle piece or frame insert should be pressed as closely as possible to the filter surface without actually making contact with the filter. The film is then drawn down onto the filter by creating a very slight suction with the sampling pump. While under this slight vacuum condition, the cassette middle piece or insert is pressed down again, then the pump is stopped. A centimeter or so of decane is gently added to the assembly to fix the two membranes. After about 30 seconds, most of the decane should be drawn through the assembly, but without pulling through any more air. It is advisable to place a liquid trap in the line to prevent the pump from flooding. Finally, the cassette is capped for transport. At this point, the sample may be moved without fear of particulate dislocation or loss from the filter, since they are now enmeshed between two protective films. As shown in FIG. 1, particulate 1 is sandwiched between collodion layer 2 and carbon coat 3 on top of NUCLEOPORE ® polycarbonate filter 4.

The filter can then be selectively dissolved and the sample can then be examined by transmission electron microscopy according to techniques well-known in the art. Examples of image quality possible with this technique are presented in FIGS. 2 through 4. These transmission electron microscopy images are taken of asbestos fibers between a carbon coat and collodion film as shown in FIG. 1. Evidence of the carbon and collodion film can be seen on careful examination of those images. The image in FIG. 2 also includes copper grid 5. Thicker or thinner films may be cast as desired for specific applications. FIGS. 2-5 pertain to the results of an air sampling with notations the same as in FIG. 1. This technique is also applicable for sampling of particulates from liquids.

The present invention has been described with reference to certain specific embodiments which have been presented for purposes of illustration. It is to be understood, however, that numerous variations of the invention can be made which are well within the scope and spirit of the invention as described in the following claims.

What is claimed is:

1. A method for collecting and preserving a sample of particulate as present in a particulate suspension, comprising:
   (a) coating a collecting substrate with an optically and/or electron transparent substance, wherein the optically and/or electron transparent substance is a carbon coating;
   (b) collecting the sample of particulate on the collecting substrate, wherein the particulate is deposited on the collecting substrate in substantially the same condition and configuration as present in the particulate suspension; and
   (c) placing an optically and/or electron transparent overlay on top of the deposited particulate, thereby retaining the deposited particulate in substantially the same condition and configuration as when the particulate was initially deposited.

2. The method according to claim 1, wherein the collecting substrate is a filter.

3. The method according to claim 2, wherein the filter is a polycarbonate or a cellulose ester acetate filter.

4. The method according to claim 1, wherein the optically and/or electron transparent overlay is a film.

5. The method according to claim 4, wherein the film is a collodion or urethane film.

6. A method for collecting and preserving a sample of particulate as present in a particulate suspension, comprising:
 (a) coating a collecting substrate with an optically and/or electron transparent substance, wherein the optically and/or electron transparent substance is a carbon coating;
 (b) collecting the sample of particulate on the collecting substrate, wherein the particulate is deposited on the collecting substrate in substantially the same condition and configuration as present in the particulate suspension; and
 (c) fixing an optically and/or electron transparent overlay on top of the deposited particulate to the collecting substrate, thereby retaining the deposited particulate in substantially the same condition and configuration as when the particulate was initially deposited.

7. The method according to claim 6, wherein the overlay is fixed by treatment with acetone.

8. The method according to claim 6, wherein the overlay is fixed by treatment with a $C_8$-$C_{18}$ alkane.

9. The method according to claim 6, wherein the collecting substrate is a filter.

10. The method according to claim 9, wherein the filter is a polycarbonate or a cellulose ester acetate filter.

11. The method according to claim 6, wherein the overlay is a film.

12. The method according to claim 11, wherein the film is a collodion or urethane film.

13. The method according to claim 6, wherein the collecting substrate is a polycarbonate filter, the $C_8$-$C_{18}$ alkane is decane, and the overlay is a collodion film.

* * * * *